United States Patent [19]

Kleiner

[11] Patent Number: 4,708,824

[45] Date of Patent: Nov. 24, 1987

[54] PROCESS FOR THE PREPARATION OF CHLORO(PHENYL)PHOSPINES

[75] Inventor: Hans-Jerg Kleiner, Kronberg/Taunus, Fed. Rep. of Germany

[73] Assignee: Hoechst Aktiengesellschaft, Frankfurt, Fed. Rep. of Germany

[21] Appl. No.: 750,030

[22] Filed: Jun. 28, 1985

[30] Foreign Application Priority Data

Jun. 30, 1984 [DE] Fed. Rep. of Germany ....... 3424182

[51] Int. Cl.$^4$ .............................................. C07F 9/52
[52] U.S. Cl. .................................. 260/543 P; 568/14; 568/17
[58] Field of Search ................. 568/14, 17; 260/543 P

[56] References Cited

U.S. PATENT DOCUMENTS

| | | | |
|---|---|---|---|
| 3,024,278 | 3/1962 | Groenweghe | 260/543 P |
| 3,094,559 | 6/1963 | Cooper | 260/543 P |
| 3,579,576 | 5/1971 | Angstadt | 568/14 X R |
| 3,932,524 | 1/1976 | Gourcez et al. | 568/14 |
| 4,521,346 | 6/1985 | Kleiner | 260/543 P |
| 4,521,347 | 6/1985 | Kleiner | 260/543 P |

FOREIGN PATENT DOCUMENTS

| | | |
|---|---|---|
| 0007508 | 9/1979 | European Pat. Off. . |
| 3216381 | 11/1983 | Fed. Rep. of Germany . |
| 3216379 | 11/1983 | Fed. Rep. of Germany . |
| 3216380 | 11/1983 | Fed. Rep. of Germany . |
| 3244031 | 5/1984 | Fed. Rep. of Germany . |
| 3313921 | 10/1984 | Fed. Rep. of Germany . |
| 362026 | 1/1973 | U.S.S.R. ............... 260/543 P |

*Primary Examiner*—Helen M. S. Sneed
*Attorney, Agent, or Firm*—Curtis, Morris & Safford

[57] ABSTRACT

Chloro(diphenyl)phosphine, $(C_6H_5)_2PCl$, is prepared by reaction of diphenylphosphinic acid chloride with triphenylphosphine at temperatures between about 300° and about 600° C. The initial P-O compound undergoes deoxygenation during the reaction.

The product of the process is useful as an intermediate in various specialized areas such as the plant-protection and polymer sectors.

9 Claims, No Drawings

PROCESS FOR THE PREPARATION OF CHLORO(PHENYL)PHOSPINES

In this context, chloro(phenyl)phosphines are understood to be the two compounds which are comprised by the general formula $$(C_6H_5)_nPCl_{3-n}$$

in which n=1 or 2
namely dichloro(phenyl)phosphine $$C_6H_5PCl_2$$

and chloro(diphenyl)phosphine $$(C_6H_5)_2PCl.$$

In the main, they are valuable intermediates in various specialist areas such as, for example, the plant-protection and polymer sectors.

Plant-protection agents are obtained by, for example, starting from dichloro(phenyl)phosphine by the route via phenylthiophosphonic dichloride $C_6H_5P(S)Cl_2$. Furthermore, for example phenylphosphonic acid $C_6H_5P(O)(OH)H$ can also be obtained in a known manner from dichloro(phenyl)phosphine, which acid is itself or in the form of its salts of considerable economic importance as a stabilizer for polyamides.

It is possible for chloro(diphenyl)phosphine to prepare, by the route via the corresponding esters of diphenylphosphinous acid $(C_6H_5)_2POR$ (R=organic radical), for example acylphosphine oxide compounds which are suitable as photoinitiators for photopolymerizable compositions (European Pat. No. A-7508).

A number of different methods are known for the preparation of chloro(phenyl)phosphines. Thus, for example, by the process described in German Pat. No. A-3,216,381 chloro(diphenyl)phosphine and dichloro(phenyl)phosphine are obtained by reaction of triphenylphosphine $(C_6H_5)_3P$ with phosphorus trichloride $PCl_3$ at temperatures between 320° and 700° C., without the addition of any catalyst; the reaction takes place in accordance with the following equation:

$$(C_6H_5)_3P + PCl_3 \rightarrow (C_6H_5)_2PCl + C_6H_5PCl_2$$

The reaction can be directed towards the chloro(diphenyl)phosphine by an excess of triphenylphosphine (molar ratio triphenylphosphine:phosphorus trichloride ≧ 2:1), and towards dichloro(phenyl)phosphine by an excess of phosphorus trichloride (molar ratio triphenylphosphine:phosphorus trichloride = 1:≧2); this is governed by the following reaction equations:

Molar ratio $$(C_6H_5)_3P:PCl_3 \geq 2:1:$$

$$(C_6H_5)_3P + PCl_3 \rightarrow 3(C_6H_5)_2PCl$$

Molar ratio $$(C_6H_5)_3P:PCl_3 = 1:\geq 2:$$

$$(C_6H_5)_3P + 2PCl_3 \rightarrow 3C_6H_5PCl_2$$

At virtually the same temperature, triphenylphosphine also reacts with dichloro(phenyl)phosphine to give chloro(diphenyl)phosphine (German Pat. No. A-3,215,379):

$$(C_6H_5)_3P + C_6H_5PCl_2 \rightarrow 2(C_6H_5)_2PCl$$

In a similar manner, phosphorus trichloride reacts with chloro(diphenyl)phosphine to give dichloro(phenyl)phosphine (German Pat. No. A-3,216,380):

$$PCl_3 + (C_6H_5)_2PCL \rightarrow 2C_6H_5PCl_2$$

In all the reactions mentioned above, a phenyl group in the P compound which has more phenyl groups is replaced by a Cl atom from the P compound which has more Cl.

The process described in German Pat. No. A-3,244,031 for the preparation of aromatic phosphorus/chlorine compounds by reaction of phosphine oxide or sulfides of the formula A)

$$(C_6H_5)_m\overset{\overset{X}{\|}}{P}Cl_{3-m} \quad (A)$$

in which
  X=O or S, and
  m=1, 2 or 3,
with P-Cl compounds of the formula (B)

$$(C_6H_5)_{3-n}PCl_n \quad (B)$$

in which n=1, 2 or 3,
at temperatures between about 330° and 700° C., is likewise based on the replacement of phenyl groups by Cl atoms.

In the case where X=0 and m=3 in the compounds of the formula (A), the compound is triphenylphosphine oxide, when n=3 in the compounds of the formula (B), the result is phosphorus trichloride. The reaction of triphenylphosphine oxide with phosphorus trichloride initially gives chloro(diphenyl)phosphine oxide (=diphenylphosphinic chloride) and dichloro(phenyl)phosphine:

$$(C_6H_5)_3\overset{\overset{O}{\|}}{P} + PCl_3 \rightarrow (C_6H_5)_2\overset{\overset{O}{\|}}{P}Cl + C_6H_5PCl_2$$

The dichloro(phenyl)phosphine can react with further triphenylphosphine oxide to give chloro(diphenyl)phosphine oxide (=diphenylphosphinic chloride) and chloro(diphenyl)phosphine:

$$(C_6H_5)_3\overset{\overset{O}{\|}}{P} + C_6H_5PCl_2 \rightarrow (C_6H_5)_2\overset{\overset{O}{\|}}{P}Cl + (C_6H_5)_2PCl$$

The more phenyl groups in the starting compounds (A) and the more Cl in the other starting compounds (B), the better the reaction takes place. No exemplary embodiment of the reaction of, for example, dichloro(phenyl)phosphine oxide (=compound of the formula (A) with X=0 and m=1; =phenylphosphonic dichloride) with chloro(diphenyl)phosphine (=compound of the formula B) with n=1) is contained in the German patent.

Aliphatic chlorophosphines can, inter alia, also be obtained by the deoxygenation of the chlorides of aliphatic P-O acids. Thus, for example, according to the process published in Soviet Certificate of Authorship 362,026, methylphosphonic dichloride is reacted with an aliphatic phosphine—in particular with tri-n-butylphosphine (n—C$_4$H$_9$)$_3$P and tri-i-amylphosphine (i—C$_5$H$_{11}$)$_3$P—at temperatures between 175° and 220° C., the oxygen of the methylphosphonic dichloride being transferred to the aliphatic phosphine. The conversion is based on the following reaction equation:

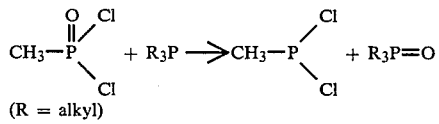

(R = alkyl)

However, if the aliphatic phosphine in this reaction is replaced by the triphenylphosphine, which is more readily accessible industrially and is cheaper, then, as our own experiments have shown, the yield of dichloro(alkyl)phosphine which is obtained is but inadequate for practical requirements (less than 30% of theory).

According to the process proposed in Patent Application P 33 13,921.0 (HOE 83/F 060), the deoxygenation with triphenylphosphine succeeds when the chlorides of P-O acids of the following formula are used as the P-O compounds which are to be deoxygenated:

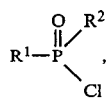

in which
R$^1$ = aromatic or heterocyclic radical, and
R$^2$ = aliphatic radical or Cl.

These are aromatic- (or heterocyclic-)aliphatic phosphinic chlorides where R$^2$ = aliphatic radical, and are aromatic (or heterocyclic) phosphonic dichlorides where R$^2$ = Cl.

Aromatic and heterocyclic dichlorophosphines, and aromatic- and heterocyclic-aliphatic monochlorophosphines, are obtained in yields between about 75 and 100% of theory by this reaction, which normally takes place at temperatures between about 100° and about 350° C.; the conversion is based on the following reaction equation:

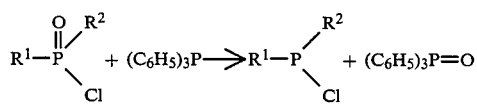

R$^1$ and R$^2$ have the abovementioned meaning.

A chloro(phenyl)phosphine can be obtained by this reaction if phenylphosphonic dichloride (=compound of the general formula indicated above, with R$^1$=C$_6$H$_5$ and R$^2$=Cl) is used as the starting compound:

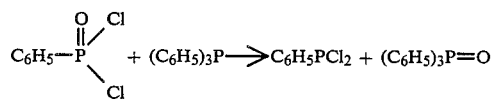

It has now been found, in a further development of this deoxygenation reaction, that it is also possible to deoxygenate diphenylphosphinic chloride (C$_6$H$_5$)$_2$P(O)Cl with triphenylphosphine to give chloro(diphenyl)phosphine; the chloro(diphenyl)phosphine can then in turn be used for the deoxygenation of the dichloride of phenylphosphonic acid to give dichloro(phenyl)phosphine.

Thus the invention relates to a process for the preparation of chloro(phenyl)phosphines of the formula

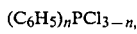

in which n=1 or 2,
which comprises the reaction of chlorides of aromatic P-O acids of the formula

in which n has the abovementioned meaning,
with triphenylphosphine in the case where n=2, and with chloro(diphenyl)phosphine in the case where n=1, at temperatures between about 300° to about 600° C. This entails the following deoxygenation reactions taking place:

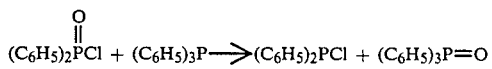

diphenylphosphinic chloride

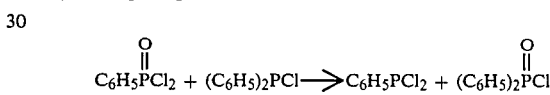

phenylphosphonic dichloride

The yields in the two individual reactions (a) and (b) are always between about 80 and 100% of theory. It was surprising that it was possible to deoxygenate in high yield the chlorides of purely aromatic P-O acids (diphenylphosphinic chloride, phenylphosphonic dichloride) using an aromatic phosphine (triphenylphosphine, chloro(diphenyl)phosphine), because it is possible only very incompletely to deoxygenate purely aliphatic phosphonic dichlorides to the corresponding dichlorophosphines using triphenylphosphine (which is aromatic). It is true that the starting materials in the individual reaction (b) (phenylphosphonic dichloride and chloro(diphenyl)phosphine) are, purely formally, included in the general formulae of the starting materials for the process according to German Pat. No. A 3,244,031; as has only now been found, by intensive investigation and repetition of this reaction, in the case where phenylphosphonic dichloride is heated with chloro(diphenyl)phosphine the C$_6$H$_5$/Cl exchange reaction which is typical for the process of the abovementioned German patent takes place to only an extremely minor extent. The reaction which takes place virtually exclusively in this instance is deoxygenation of the phenylphosphonic dichloride.

The starting compounds for the process according to the invention are diphenylphosphinic chloride and triphenylphosphine or phenylphosphonic dichloride and chloro(diphenyl)phosphine.

Diphenylphosphinic chloride is obtained by, for example, alkaline hydrolysis of triphenylphosphinic oxide, followed by chlorination with, for example, SOCl$_2$.

Triphenylphosphine is a readily available commercial product whose preparation hardly needs to be reported.

Phenylphosphonic dichloride is readily obtainable by, for example, reaction of bromobenzene with triethyl phosphite/Ni catalyst, followed by the action of $COCl_2$ or $SOCl_2$.

Chloro(diphenyl)phosphine is accessible by deoxygenation of diphenylphosphinic chloride in accordance with individual reaction (a) of the process according to the invention or, where appropriate, by the methods of the state of the art mentioned in the introduction.

To carry out the process according to the invention, the starting compounds diphenylphosphinic chloride and triphenylphosphine or phenylphosphonic dichloride and chloro(diphenyl)phosphine are first mixed. Homogeneous mixtures are produced, where appropriate, only at elevated temperatures, especially between diphenylphosphinic chloride and triphenylphosphine. The components are advantageously employed in the molar ratio of about 1:1. However, excesses of one or other of the components are possible.

In the temperature range between about 300° and 500° C., preferably between about 350° and 450° C., the mixture of the starting materials is preferably reacted under elevated pressure, in particular under the (autogenous) pressure set up in a closed reaction vessel. In this case, the reaction time is between about one and thirty hours.

In the temperature range between about 500° and 600° C., preferably between about 500° and 550° C., the mixture of the starting materials is preferably reacted under atmospheric pressure. It is advantageous when this process variant is carried out to meter the mixture of starting materials into a heated reaction zone using a metering device. An example of a suitable reaction zone is an electrically heated tube. The reaction mixture emerging from the reaction zone is collected in a receiver. It may be advantageous for this to be cooled. In this case, the reaction times are of the order of only seconds or minutes in practice.

It may be advantageous to carry out the reaction under an inert gas atmosphere (nitrogen, argon, etc.), especially with the process variant which is carried out at about 500° to 600° C.

The process can be carried out either continuously or discontinuously.

The reaction mixtures are worked up in a customary manner, for example using distillation processes. When triphenylphosphine oxide is produced, it is also possible to make use of its tendency to crystallize to remove the main amount of the triphenylphosphine oxide which is produced (where appropriate using a suitable solvent) as crystals.

The invention represents a considerable enrichment of technology because the starting materials are readily accessible, the reaction is straightforward to carry out, and the yields of chloro(phenyl)phosphines are high.

The examples which follow are intended to illustrate the invention further. The examples of the invention are followed by a comparison example which shows that only relatively little dichlorophosphine is produced in the reaction of an aliphatic phosphonic dichloride with triphenylphosphine.

EXAMPLES OF THE INVENTION

Example 1

20 g (=0.0846 mol) of diphenylphosphinic chloride and 30 g (=0.115 mol) of triphenylphosphine were maintained at 400° C. in a 90 ml pressure tube for 20 hours. The resulting reaction mixture was subjected to initial distillation under 26.6 Pa, with a short column, up to an internal temperature of about 185° C. The distillate amounted to 32 g. On the basis of a $^{31}P$-NMR spectrum, it contained, inter alia, 30.1% chloro(diphenyl)-phosphine and 15% diphenylphosphinic chloride. At a conversion of 76%, this corresponds to a yield of 81% of theory based on diphenylphosphinic chloride used.

Example 2

20 g (=0.1025 mol) of phenylphosphonic dichloride and 40 g (=0.1815 mol) of chloro(diphenyl)phosphine were maintained at 370° C. in a 90 ml pressure tube for 20 hours. The resulting reaction mixture was distilled under 26.6 Pa, without a column, up to an internal temperature of about 200° C. 55 g of distillate were obtained by this. On the basis of a $^{31}P$-NMR spectrum, the distillate was composed of 30.9% dichloro(phenyl)phosphine, 28.9% chloro(diphenyl)phosphine, 31.8% diphenylphosphinic chloride, 3.8% unreacted phenylphosphonic dichloride, 1.5% triphenylphosphine oxide and 3.1% triphenylphosphine. The individual components indicated can be separated by distillation, 30.9% of 55 g resulting in about 17 g of dichloro(phenyl)phosphine. Without taking into account the phenylphosphonic dichloride which can be recovered, this results in a yield of about 93% of theory based on phenylphosphonic dichloride used.

Comparison Example 67.2 g (=0.46 mol) of ethylphosphonic dichloride and 60 g (=0.23 mol) of triphenylphosphine were stirred under gentle reflux at 195° C., under an atmosphere of nitrogen. Under reflux conditions, the internal temperature decreased to 185° C. over the course of 22 hours. After cooling, the mixture was distilled under 5.07 kPa. This resulted in about 8 g of dichloro(ethyl)phosphine being obtained, which distilled over at a temperature of 26° C. and condensed in a cooled receiver, and then 37 g of ethylphosphonic dichloride being obtained, which distilled over at a temperature of 80° C. with the internal temperature rising to 200° C. The distillation residue was then distilled under 0.1 kPa. This resulted in about 45 g of unreacted triphenylphosphine being obtained.

The yield of dichloro(ethyl)phosphine is about 27% of theory based on triphenylphosphine used.

I claim:

1. A process for the preparation of chloro(diphenyl)phosphine which comprises reacting diphenylphosphinic (acid) chloride with triphenylphosphine to deoxygenate the diphenylphosphinic (acid) chloride at a temperature between about 300° and about 600° C.

2. The process as claimed in claim 1, wherein the starting materials are used in a molar ratio of about 1:1.

3. A process for the preparation of chloro(diphenyl)phosphine which comprises reacting under elevated pressure diphenylphosphinic (acid) chloride with triphenylphosphine to deoxygenate the diphenylphosphinic (acid) chloride at a temperature between about 300° and about 500° C.

4. The process as claimed in claim 1, wherein the reaction is carried out at a temperature between about 500° and about 600° C., under atmospheric pressure.

5. The process as claimed in claim 3, wherein the reaction is carried out under an inert gas.

6. The process as claimed in claim 3, wherein the reaction is carried out under elevated autogenous pressure.

7. The process as claimed in claim 3, wherein the reaction is carried out at a temperature between about 350° and 450° C. for a time between about one and 30 hours.

8. The process as claimed in claim 4, wherein the reaction is carried out under an inert gas.

9. The process as claimed in claim 4, wherein the reaction is carried out at a temperature between about 500° and 550° C.

* * * * *